US007510857B2

(12) United States Patent
Brumm

(10) Patent No.: US 7,510,857 B2
(45) Date of Patent: Mar. 31, 2009

(54) THERMOSTABLE CELLULASE AND METHODS OF USE

(75) Inventor: Phillip Brumm, Fitchburg, WI (US)

(73) Assignee: C5-6 Technologies, Inc., Middleton, WI (US)

( * ) Notice: Subject to any disclaimer, the term of this patent is extended or adjusted under 35 U.S.C. 154(b) by 0 days.

(21) Appl. No.: 11/741,254

(22) Filed: Apr. 27, 2007

(65) Prior Publication Data

US 2007/0256197 A1 Nov. 1, 2007

Related U.S. Application Data

(60) Provisional application No. 60/745,976, filed on Apr. 28, 2006.

(51) Int. Cl.
*C12P 19/14* (2006.01)
*C12P 7/06* (2006.01)
*C12P 7/56* (2006.01)
*C12N 9/24* (2006.01)
*C08B 37/00* (2006.01)
*D21C 1/00* (2006.01)
*C07H 21/04* (2006.01)

(52) U.S. Cl. ........................ 435/99; 435/139; 435/150; 435/161; 435/200; 435/201; 435/274; 435/277; 435/419; 435/463; 435/209; 435/165; 435/105; 435/155; 435/163; 536/23.2

(58) Field of Classification Search ........................ None
See application file for complete search history.

(56) References Cited

U.S. PATENT DOCUMENTS

| | | | |
|---|---|---|---|
| 4,540,664 | A | 9/1985 | Johnson et al. |
| 6,190,189 | B1 | 2/2001 | Li et al. |
| 6,204,012 | B1 | 3/2001 | Hellmuth et al. |
| 6,268,196 | B1 | 7/2001 | Fowler et al. |
| 6,680,426 | B2 | 1/2004 | Daniell et al. |
| 7,033,627 | B2 | 4/2006 | Van Ooyen et al. |

OTHER PUBLICATIONS

Whisstock et al., Prediction of protein function from protein sequence. Q. Rev. Biophysics., 2003, vol. 36 (3): 307-340.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol., 2001, vol. 183 (8): 2405-2410.*
Witkowski et al., Conversion of b-ketoacyl synthase to a malonyl decarboxylase by replacemnt of the active-site cysteine with glutamine. Biochemistry, 1999, vol. 38: 11643-11650.*
Bayer, E.A. et al., "Cellulosomes—structure and ultrastructure," J. Struct. Biol. (1998) 124:221-234.
Bergquist, P.L. et al., "Molecular diversity of thermophilic cellulolytic and hemicellulolytic bacteria," FEMS Micro. Ecol. (1999) 28:99-110.
Breves, R. et al., "Genes encoding two different beta-glucosidases of *Thermoanaerobacter brockii* are clustered in a common operon," Appl. Env. Microbiol. (1997) 63(10):3902-3910.
Brumm, P. et al., "Novel endoglucanase of *Clostridium thermocellum*," Lucigen (Apr. 30, 2006), 1 page.
Doi, R.H. et al., "Cellulosomes: plant-cell-wall-degrading enzyme complexes," Nature Reviews (2004) 2:541-551.
Kengen, S.W.M. et al., "Purification and characterization of an extremely thermostable beta-glucosidase from the hyperthermophilic archaeon *Pyrococcus furiosus*," Eur. J. Biochem. (1993) 213:305-312.
Lynd, L.R. et al., "Microbial cellulose utilization: fundamentals and biotechnology," Microbiol. Mol. Biol. Rev. (2002) 66(3):506-577.
Mitchinson, C., "Improved cellulases for the biorefinery: a review of Genencor's progress in the DOE subcontract for cellulase cost reduction for bioethanol," Stanford GCEP Biomass Energy Workshop, Apr. 2004.
National Renewable Energy Laboratory, "NREL getting extra 'corn squeezins' cooperative agreement uses cellulosic fiber to get more ethanol from corn," NREL Technology Brief (Nov. 1993) 4 pages.
National Renewable Energy Laboratory, "Range of biorefinery concepts," (Sep. 9, 2006) 1 page.
Saville, B.A. et al., "Effect of cellulase supplementation on cookline operation in a dry mill ethanol plant," Presented at the 27th Symposium on Biotechnology for Fuels and Chemicals, University of Toronto, May 1, 2005.
Wang, X. et al., "Structure basis for thermostability of beta-glycosidase from the thermophilic eubacterium thermus nonproteolyticus HG102," J. Bacteriol. (2003) 185(14):4248-4255.
Wright, R.M. et al., "Cloning, characterization, and nucleotide sequence of a gene encoding Microbispora bispora BgIB, a thermostable beta-glucosidase expressed in *Escherichia coli*," App. Env. Microbiol. (1992) 58(11):3455-3465.
Zverlov, V.V. et al., "*Thermotoga neopolitana* bgIB gene, upstream of IamA, encodes a highly thermostable beta-glucosidase that is a laminaribiase," Microbiology (1997) 143:3537-3542.

* cited by examiner

*Primary Examiner*—Rebecca E. Prouty
*Assistant Examiner*—Ganapathirama Raghu
(74) *Attorney, Agent, or Firm*—Michael Best & Friedrich LLP

(57) ABSTRACT

A *Clostridium thermocellum* thermostable cellulase enzyme with both endocellulase activity and exocellulase activity that is able to degrade cellulose in the absence of scaffolding and other cellulosomic proteins is provided. The use of the enzyme to degrade cellulosic materials to soluble sugars is also provided.

20 Claims, 2 Drawing Sheets

SEQUENCE LISTING

<160> NUMBER OF SEQ ID NOS: 7

<210> SEQ ID NO 1
<211> LENGTH: 494
<212> TYPE: PRT
<213> ORGANISM: Clostridium thermocellum

<400> SEQUENCE: 1

Pro Asn Asn Asp Asp Trp Leu His Val Glu Gly Asn Lys Ile Val Asp
1               5                   10                  15

Met Tyr Gly Asn Gln Val Trp Leu Thr Gly Cys Asn Trp Phe Gly Phe
            20                  25                  30

```
Asn Thr Gly Thr Asn Val Phe Asp Gly Val Trp Ser Cys Asn Met Arg
        35                  40                  45
Glu Ala Leu Lys Gly Met Ala Asp Arg Gly Ile Asn Phe Leu Arg Ile
 50                  55                  60
Pro Ile Ser Thr Glu Leu Leu Tyr Gln Trp Ser Gln Gly Ile Tyr Pro
 65                  70                  75                  80
Lys Ala Asn Val Asn Asp Phe Val Asn Pro Glu Leu Lys Gly Lys Asn
                 85                  90                  95
Ser Leu Glu Leu Phe Asp Phe Ala Val Gln Cys Cys Lys Glu Phe Gly
                100                 105                 110
Ile Lys Ile Met Val Asp Ile His Ser Pro Ala Thr Asp Ala Met Gly
        115                 120                 125
His Met Tyr Pro Leu Trp Tyr Asp Gly Gln Phe Thr Thr Glu Ile Trp
        130                 135                 140
Ile Ser Thr Leu Glu Trp Leu Thr Glu Arg Tyr Lys Asn Asp Asp Thr
145                 150                 155                 160
Ile Leu Ala Leu Asp Leu Lys Asn Glu Pro His Gly Thr Pro Gly Ser
                165                 170                 175
Glu Leu Met Ala Lys Trp Asp Gly Ser Thr Asp Leu Asn Asn Trp Lys
                180                 185                 190
His Ala Ala Glu Thr Cys Ala Lys Arg Ile Leu Ala Ile Asn Pro Asn
        195                 200                 205
Ile Leu Ile Val Val Glu Gly Val Glu Val Tyr Pro Lys Pro Gly Tyr
        210                 215                 220
Asp Tyr Thr Ala Val Asp Glu Trp Gly Lys Glu Ser Lys Tyr Phe Tyr
225                 230                 235                 240
Asn Trp Trp Gly Gly Asn Leu Arg Gly Val Arg Asp Tyr Pro Ile Asp
                245                 250                 255
Leu Gly Lys His Gln Lys Gln Leu Val Tyr Ser Pro His Asp Tyr Gly
                260                 265                 270
Pro Leu Val His Lys Gln Pro Trp Phe Tyr Glu Gly Phe Asn Lys Glu
        275                 280                 285
Thr Leu Tyr Asn Asp Cys Trp Arg Asp Asn Trp Ala Tyr Ile His Glu
        290                 295                 300
Glu Asn Ile Ala Pro Leu Ile Val Gly Glu Trp Gly Gly Phe Met Asp
305                 310                 315                 320
Arg Gly Asp Asn Glu Lys Trp Met Lys Ala Leu Arg Asp Tyr Met Ile
                325                 330                 335
Glu Asn Lys Ile Ser His Thr Phe Trp Cys Tyr Asn Ala Asn Ser Gly
                340                 345                 350
Asp Thr Gly Gly Leu Val Tyr Tyr Asp Phe Ile Thr Trp Asp Glu Glu
        355                 360                 365
Lys Tyr Ala Leu Leu Lys Pro Ala Leu Trp Gln Thr Glu Asp Gly Lys
        370                 375                 380
Phe Ile Gly Leu Asp His Gln Ile Pro Leu Gly Ser Asn Gly Ile Thr
385                 390                 395                 400
Val Thr Glu Tyr Tyr Gly Gly Tyr Ile Pro Glu Pro Ser Pro Thr Ala
                405                 410                 415
Thr Val Pro Asp Val Pro Thr Pro Ser His Ser Phe Glu Ile Glu Lys
                420                 425                 430
Gly Asp Val Asn Gly Asp Gly Asn Val Asn Ser Thr Asp Val Val Trp
        435                 440                 445
```

```
Leu Arg Arg Phe Leu Leu Lys Leu Val Glu Asp Phe Pro Val Pro Ser
    450                 455                 460

Gly Lys Gln Ala Ala Asp Met Asn Asp Gly Asn Ile Asn Ser Thr
465                 470                 475                 480

Asp Met Ile Ala Leu Lys Arg Lys Val Leu Lys Ile Pro Ile
                485                 490
```

```
<210> SEQ ID NO 2
<211> LENGTH: 1482
<212> TYPE: DNA
<213> ORGANISM: Clostridium thermocellum

<400> SEQUENCE: 2
```

| | | | | | |
|---|---|---|---|---|---|
| ccgaacaatg | acgactggct | gcatgttgaa | ggtaacaaaa | tagtggacat | gtacggtaat | 60 |
| caggtctggc | tgaccggctg | caactggttt | ggattcaata | ccggtaccaa | tgtgtttgac | 120 |
| ggagtatgga | gctgcaatat | gagagaagcc | ctcaaggggta | tggcggacag | aggaataaat | 180 |
| tttttgagaa | tacctatttc | aacagaattg | ctgtatcaat | ggtctcaagg | aatatatccc | 240 |
| aaagcaaatg | ttaatgattt | tgtaaatccg | gagctgaaag | gaaagaacag | ccttgagctt | 300 |
| tttgactttg | ccgttcagtg | ctgcaaagaa | ttcggaataa | agataatggt | ggatatacac | 360 |
| agtccggcaa | cagatgccat | ggggcatatg | tatccttat | ggtatgacgg | tcaatttaca | 420 |
| acagagatat | ggatttcaac | tttggagtgg | ttgacgaaa | gatataaaaa | tgatgacaca | 480 |
| attcttgcac | tggaccttaa | aaatgagcct | cacggcaccc | cgggcagcga | attaatggcc | 540 |
| aaatgggatg | gttccacgga | tttgaacaac | tggaagcatg | ctgctgaaac | atgcgcaaag | 600 |
| agaatccttg | caataaatcc | gaatattctt | attgtggtag | aaggagtgga | agtttatcca | 660 |
| aagcctggct | atgattatac | cgcagtggac | gaatggggaa | aagagagtaa | atatttctat | 720 |
| aactggtggg | gaggaaattt | aagaggagtc | agggattatc | ccattgacct | tggcaagcat | 780 |
| cagaagcagc | ttgtatactc | acctcacgat | tacggtcccc | tcgtacataa | acaaccttgg | 840 |
| ttctatgaag | gctttaacaa | agaaactttg | tataatgatt | gctggagaga | taactgggca | 900 |
| tacatacacg | aggaaaacat | cgctcctctg | atagtgggtg | aatggggagg | tttcatggac | 960 |
| cgcggagaca | acgagaaatg | gatgaaagcg | ctgagagatt | atatgattga | gaataaaata | 1020 |
| tcccacactt | tttggtgcta | taatgcaaat | tccggtgata | ccggaggact | tgtatactat | 1080 |
| gattttatta | cctgggacga | agaaaaatat | gctcttctga | agcctgcatt | atggcagaca | 1140 |
| gaggacggaa | agtttatagg | ccttgaccat | cagataccte | ttggttcaaa | tggaattacc | 1200 |
| gtaactgaat | attatggcgg | ctatattccg | gaaccgtcac | cgactgctac | tgttccagac | 1260 |
| gtaccgacac | cgtcgcattc | tttcgaaata | gagaaggggg | atgtaaacgg | tgacggtaat | 1320 |
| gttaattcaa | cagatgttgt | atggcttagg | agatttttgc | taaaattggt | cgaggatttt | 1380 |
| cctgtacctt | ccggaaaaca | ggcggcggat | atgaatgatg | acgggaatat | caattctacc | 1440 |
| gatatgatag | ccttaaagag | gaaagtgctt | aaaataccaa | ta | | 1482 |

```
<210> SEQ ID NO 3
<211> LENGTH: 33
<212> TYPE: DNA
<213> ORGANISM: Unknown
<220> FEATURE:
<223> OTHER INFORMATION: CTH10H6 Left Primer
<400> SEQUENCE: 3
ccgaacaatg acgactggct gcatgttgaa ggt                                33
```

-continued

```
<210> SEQ ID NO 4
<211> LENGTH: 45
<212> TYPE: DNA
<213> ORGANISM: Unknown
<220> FEATURE:
<223> OTHER INFORMATION: CTH10H6 Right Primer

<400> SEQUENCE: 4
tcttctctgc ggccgcttat attggtattt taagcacttt cctct              45

<210> SEQ ID NO 5
<211> LENGTH: 526
<212> TYPE: PRT
<213> ORGANISM: Clostridium thermocellum

<400> SEQUENCE: 5

Met Arg Lys Val Lys Ala Leu Leu Leu Gly Leu Ile Val Leu Ala Val
1               5                   10                  15

Ala Leu Leu Pro Thr Val Ser Phe Lys Ser Pro Thr Val Ala Ala Asp
            20                  25                  30

Pro Asn Asn Asp Asp Trp Leu His Val Glu Gly Asn Lys Ile Val Asp
        35                  40                  45

Met Tyr Gly Asn Gln Val Trp Leu Thr Gly Cys Asn Trp Phe Gly Phe
    50                  55                  60

Asn Thr Gly Thr Asn Val Phe Asp Gly Val Trp Ser Cys Asn Met Arg
65                  70                  75                  80

Glu Ala Leu Lys Gly Met Ala Asp Arg Gly Ile Asn Phe Leu Arg Ile
                85                  90                  95

Pro Ile Ser Thr Glu Leu Leu Tyr Gln Trp Ser Gln Gly Ile Tyr Pro
            100                 105                 110

Lys Ala Asn Val Asn Asp Phe Val Asn Pro Glu Leu Lys Gly Lys Asn
        115                 120                 125

Ser Leu Glu Leu Phe Asp Phe Ala Val Gln Cys Cys Lys Glu Phe Gly
    130                 135                 140

Ile Lys Ile Met Val Asp Ile His Ser Pro Ala Thr Asp Ala Met Gly
145                 150                 155                 160

His Met Tyr Pro Leu Trp Tyr Asp Gly Gln Phe Thr Thr Glu Ile Trp
                165                 170                 175

Ile Ser Thr Leu Glu Trp Leu Thr Glu Arg Tyr Lys Asn Asp Asp Thr
            180                 185                 190

Ile Leu Ala Leu Asp Leu Lys Asn Glu Pro His Gly Thr Pro Gly Ser
        195                 200                 205

Glu Leu Met Ala Lys Trp Asp Gly Ser Thr Asp Leu Asn Asn Trp Lys
    210                 215                 220

His Ala Ala Glu Thr Cys Ala Lys Arg Ile Leu Ala Ile Asn Pro Asn
225                 230                 235                 240

Ile Leu Ile Val Val Glu Gly Val Glu Val Tyr Pro Lys Pro Gly Tyr
                245                 250                 255

Asp Tyr Thr Ala Val Asp Glu Trp Gly Lys Glu Ser Lys Tyr Phe Tyr
            260                 265                 270

Asn Trp Trp Gly Gly Asn Leu Arg Gly Val Arg Asp Tyr Pro Ile Asp
        275                 280                 285

Leu Gly Lys His Gln Lys Gln Leu Val Tyr Ser Pro His Asp Tyr Gly
    290                 295                 300

Pro Leu Val His Lys Gln Pro Trp Phe Tyr Glu Gly Phe Asn Lys Glu
305                 310                 315                 320
```

```
Thr Leu Tyr Asn Asp Cys Trp Arg Asp Asn Trp Ala Tyr Ile His Glu
                325                 330                 335

Glu Asn Ile Ala Pro Leu Ile Val Gly Glu Trp Gly Gly Phe Met Asp
            340                 345                 350

Arg Gly Asp Asn Glu Lys Trp Met Lys Ala Leu Arg Asp Tyr Met Ile
        355                 360                 365

Glu Asn Lys Ile Ser His Thr Phe Trp Cys Tyr Asn Ala Asn Ser Gly
    370                 375                 380

Asp Thr Gly Gly Leu Val Tyr Tyr Asp Phe Ile Thr Trp Asp Glu Glu
385                 390                 395                 400

Lys Tyr Ala Leu Leu Lys Pro Ala Leu Trp Gln Thr Glu Asp Gly Lys
                405                 410                 415

Phe Ile Gly Leu Asp His Gln Ile Pro Leu Gly Ser Asn Gly Ile Thr
            420                 425                 430

Val Thr Glu Tyr Tyr Gly Gly Tyr Ile Pro Glu Pro Ser Pro Thr Ala
        435                 440                 445

Thr Val Pro Asp Val Pro Thr Pro Ser His Ser Phe Glu Ile Glu Lys
    450                 455                 460

Gly Asp Val Asn Gly Asp Gly Asn Val Asn Ser Thr Asp Val Val Trp
465                 470                 475                 480

Leu Arg Arg Phe Leu Leu Lys Leu Val Glu Asp Phe Pro Val Pro Ser
                485                 490                 495

Gly Lys Gln Ala Ala Asp Met Asn Asp Asp Gly Asn Ile Asn Ser Thr
            500                 505                 510

Asp Met Ile Ala Leu Lys Arg Lys Val Leu Lys Ile Pro Ile
        515                 520                 525

<210> SEQ ID NO 6
<211> LENGTH: 1581
<212> TYPE: DNA
<213> ORGANISM: Clostridium thermocellum

<400> SEQUENCE: 6
atgagaaagg ttaaggcctt gttgttggga ttgattgtat tggctgtagc tttgttacct     60
acagtgtcct ttaagtcacc gactgttgcg gccgatccga acaatgacga ctggctgcat    120
gttgaaggta caaaatagt ggacatgtac ggtaatcagg tctggctgac cggctgcaac     180
tggtttggat tcaataccgg taccaatgtg tttgacggag tatggagctg caatatgaga    240
gaagccctca agggtatggc ggacagagga ataaattttt tgagaatacc tatttcaaca    300
gaattgctgt atcaatggtc tcaaggaata tatcccaaag caaatgttaa tgattttgta    360
aatccggagc tgaaaggaaa gaacagcctt gagcttttg actttgccgt tcagtgctgc    420
aaagaattcg aataaagat aatggtggat atacacagtc cggcaacaga tgccatgggg    480
catatgtatc ctttatggta tgacggtcaa tttacaacag atatgat ttcaactttg     540 gagtggttga cggaaagata taaaaatgat gacacaattc ttgcactgga ccttaaaaat    600
gagcctcacg gcacccc ggg cagcgaatta atggccaaat gggatggttc acggatttg    660 aacaactgga agcatgctgc tgaaacatgc gcaaagagaa tccttgcaat aaatccgaat    720
attcttattg tggtagaagg agtggaagtt tatccaaagc ctggctatga ttataccgca    780
gtggacgaat ggggaaaaga gagtaaatat ttctataact ggtggggagg aaatttaaga    840
ggagtcaggg attatcccat tgaccttggc aagcatcaga agcagcttgt atactcacct    900
cacgattacg gtccc ctcgt acataaacaa ccttggttct atgaaggctt taacaaagaa    960
```

-continued

```
actttgtata atgattgctg gagagataac tgggcataca tacacgagga aaacatcgct   1020
cctctgatag tgggtgaatg gggaggtttc atggaccgcg gagacaacga gaaatggatg   1080
aaagcgctga gagattatat gattgagaat aaaatatccc acactttttg gtgctataat   1140
gcaaattccg gtgataccgg aggacttgta tactatgatt ttattacctg ggacgaagaa   1200
aaatatgctc ttctgaagcc tgcattatgg cagacagagg acggaaagtt tataggcctt   1260
gaccatcaga tacctcttgg ttcaaatgga attaccgtaa ctgaatatta tggcggctat   1320
attccggaac cgtcaccgac tgctactgtt ccagacgtac cgacaccgtc gcattctttc   1380
gaaatagaga aggggggatgt aaacggtgac ggtaatgtta attcaacaga tgttgtatgg   1440
cttaggagat ttttgctaaa attggtcgag gattttcctg taccttccgg aaaacaggcg   1500
gcggatatga atgatgacgg gaatatcaat tctaccgata tgatagcctt aaagaggaaa   1560
gtgcttaaaa taccaatata a                                             1581
```

<210> SEQ ID NO 7
<211> LENGTH: 9
<212> TYPE: PRT
<213> ORGANISM: Unknown
<220> FEATURE:
<223> OTHER INFORMATION: Affinity tag from pTACST3 NotI blunt vector

<400> SEQUENCE: 7

```
Met Thr Gln Asp Pro Ser Arg Val Gly
1               5
```

THERMOSTABLE CELLULASE AND METHODS OF USE

CROSS-REFERENCE TO RELATED APPLICATIONS

This application claims benefit of priority under 35 USC §119 to U.S. Provisional Application Ser. No. 60/745,976, filed Apr. 28, 2006, incorporated herein by reference in its entirety.

INTRODUCTION

The invention relates generally to the fields of microbiology and enzymology. More particularly, the invention relates to a thermostable cellulase purified from *Clostridium thermocellum*, and methods of using the thermostable cellulase.

Microbial cellulases represent an enormous range of proteins with widely varying specificities, cleavage patterns, and operating parameters. Among the cellulose-degrading enzymes, there are endo-acting cellulases that cleave at internal sites on the cellulose chain, exo-acting cellulases that cleave fragments from the ends of the cellulose chain, and beta-glucosidases that hydrolyze soluble fragments to glucose. The diversity of cellulases is demonstrated by their presence in seven Glycoside Hydrolase Families (Families 1, 5, 6, 7, 9, 10, and 48). Generally, cellulase-degrading enzymes produced by aerobic bacteria are soluble, while those produced by anaerobic bacteria are bound in large, multicomponent extracellular enzyme complexes called cellulosomes.

Thermophilic, cellulase-producing microbes have been isolated and identified. In particular, thermophiles capable of growing at 70° C. or higher known to produce cellulase include both aerobes (*Caldibacillus cellovorans*, *Rhodothermus marinus* and *Acidothermus cellulolyticus*) and anaerobes (*Anaerocellum thermophilum*, *Caldicellulosiruptor saccharolyticus*, *Clostridium thermocellum*, *Fervidobacterium islandicum*, *Spirochaetta thermophila*, *Thermotoga maritime* and *Pyrocccus furiosus*).

Despite the fact that several thermophilic microorganisms are known to produce cellulases, there remains no source of thermostable cellulase suitable for commercial applications. The available products are mixtures of fungal cellulases that have effective temperature ranges of 20° C. to 50° C. Much of the research on cellulases has focused on fungal cellulase systems, particularly the cellulytic system of *Trichoderma reesei*. This multi-component enzyme system has many benefits, including the ability to produce high yields of glucose from acid-treated cellulose. However, the cellulase enzymes from this organism are not stable for extended periods of time at high temperatures (greater than 60° C.), requiring use at temperatures below 40° C. Some success has been reported in improving the thermostability of the cellulase product by either site-directed mutagenesis or by cloning of more thermostable endoglucanases into *T. reesei*. However, the improved *T. reesei* enzyme products remain unsuitable for use with other enzymes in starch liquefaction, and it is unlikely that the thermostability of all components could ever be increased sufficiently for the product to work under those conditions. An additional problem with *T. reesei* enzyme products is the requirement for extensive pretreatment of the cellulosic materials before use of the enzymes. To obtain adequate conversion, the cellulose must be first treated with acid, high temperature steam, ammonia, or other extreme processing conditions to break down the crystal structure of the cellulose. While these pretreatments may be acceptable for use with cellulosic materials, these pretreatments are not practical within the processes currently used in the production of bioethanol from cellulosic materials, among other commercial applications.

*Clostridium thermocellum*, an anaerobic thermophile that produces both soluble, cellulose-degrading enzymes and cellulosomal cellulases, has been a subject of study for decades. However, many of the *Clostridium thermocellum* cellulases require the presence of additional scaffoldin proteins to assemble correctly into a cell-bound system to degrade insoluble cellulose into soluble sugars. As described in U.S. Pat. No. 4,540,644, these cellulosome-associated enzymes are active against both crystalline cellulose and non-crystalline cellulose, but require the use of calcium to function and a reducing agent, such as dithiothreitol, in order to exhibit optimal activity.

SUMMARY OF THE INVENTION

The inventor has discovered that a previously uncharacterized soluble thermostable cellulase purified from *Clostridium thermocellum* does not require scaffoldin proteins and exhibits both endo- and exo-glucanase activities. In addition, the cellulase is stable over a broad temperature range, permitting its use in various industrial applications in which high temperatures preclude the use of non-thermostable cellulases.

Accordingly, in one aspect, the invention provides a purified thermostable cellulase comprising an amino acid sequence having at least about 80% identity to SEQ ID NO: 1. The cellulase exhibits endoglucanase or exoglucanase activity, or may exhibit both activities. The cellulase is active in soluble form. In other aspects, the invention provides a polynucleotide construct which includes a polynucleotide encoding the cellulase operably connected to a promoter, and a recombinant host cell which includes the polynucleotide construct.

In another aspect, the invention provides a transgenic plant which includes a polynucleotide construct encoding the thermostable cellulase.

In yet another aspect, the invention provides a composition which includes the thermostable cellulase. Additional components of the composition may include one or more of an alpha-amylase, a glucoamylase and a β-glucosidase.

In still another aspect, the invention provides a method of producing at least one cellulose byproduct. The method includes contacting a cellulosic material with the cellulase.

In a further aspect, the invention provides a method of producing ethanol including steps of contacting a cellulosic material with the cellulase to produce cellobiose, contacting the cellobiose with a β-glucosidase to produce glucose, and fermenting the glucose to produce ethanol.

DETAILED DESCRIPTION OF ILLUSTRATIVE EMBODIMENTS

Figure 1:
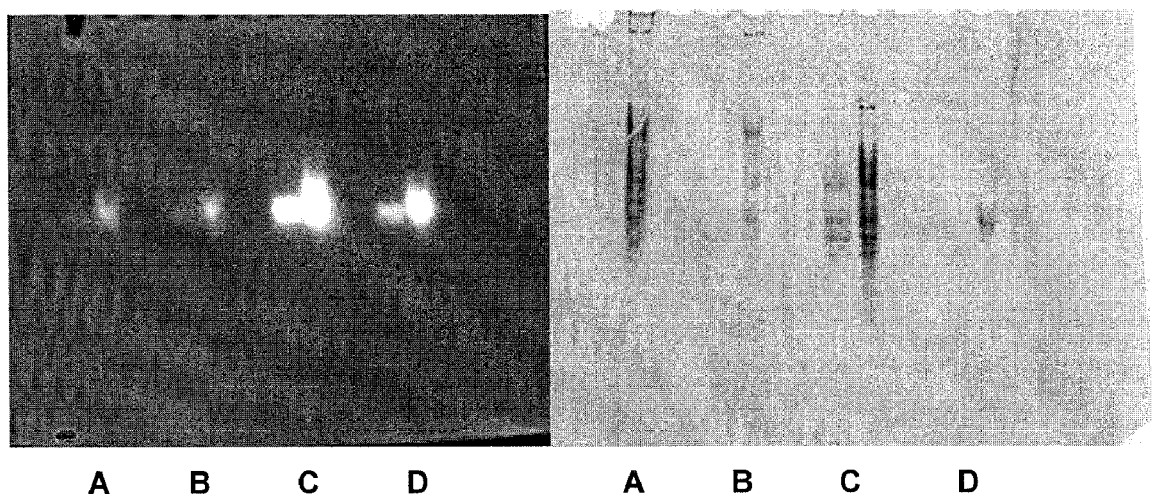
FIG. 1 is a photograph of a native gel showing cellulase activity of the enzyme expressed and purified as described in the Examples.

Cellulose-containing plant cell walls provide an abundant and renewable source of glucose, pentoses and other small carbon compounds, many of which have significant commercial value. For example, glucose is particularly valuable as feedstock for yeast in the production of bioethanol. Other commercially valuable byproducts of enzymatic conversion of cellulosic materials may be used in the manufacture of chemical products such as plastics, solvents, chemical intermediates, phenolics, adhesives, furfural, fatty acids, acetic acid, carbon black, paints, dyes, pigments, inks and detergents, in the production of power, and in food and feed products. Accordingly, there is substantial interest in the development of improved techniques for microbial enzymatic processing of cellulosic materials. As used herein, "cellulosic materials" are materials that include cellulose, cellulose derivatives, modified cellulose, or combinations thereof.

A previously undescribed enzyme was purified from *Clostridium thermocellum* by the inventor and found to exhibit cellulase activity. Accordingly, in one embodiment, the invention provides a purified thermostable cellulase having the amino acid sequence of SEQ ID NO:1. The cellulase consisting of the specific sequence of 495 amino acids shown in SEQ ID NO: 1 is referred to herein as "Cth10H6." This cellulase has a predicted molecular weight of about 57 kDa.

Purified cellulases of the invention are thermostable. As used herein a "thermostable" enzyme, including a thermostable cellulase, means that at least 70% of the enzyme's activity is retained when the enzyme is incubated at 60° C. in a suitable medium for 60 minutes. Purified cellulases of the invention exhibit activity in soluble form, i.e., independent of association with a cellulosome or related proteins such as scaffolding. As will be appreciated, the cellulases described herein may be useful in any research or commercial context and are not limited according to their potential uses.

As used herein, the term "purified" refers to material that is substantially or essentially free from components which normally accompany it in its native state. Purity of a polypeptide species is typically determined using analytical chemistry techniques such as polyacrylamide gel electrophoresis or high performance liquid chromatography. A polypeptide that is the predominant species present in a preparation is substantially purified. The term "purified" denotes that a preparation containing the polypeptide may give rise to essentially one band in an electrophoretic gel, detected by, for example, staining with Coomassie Blue R-250. Suitably, cellulases of the invention are at least about 85% pure, more suitably at least about 95% pure, and most suitably at least about 99% pure.

Purified cellulases of the invention suitably have an amino acid sequence having at least about 80% identity, more suitably at least about 85% identity, more suitably at least about 90% identity, more suitably at least about 95% identity, and most suitably at least about 98% or 99% identity, to the amino acid sequences provided in SEQ ID NO:1 Percent identity may be determined using the algorithm of Altschul et al., Nucleic Acids Res. 25:3389-3402 (1997) Such algorithm is incorporated into the BLASTP program, which may be used to obtain amino acid sequences homologous to a reference polypeptide, as is known in the art. As will be appreciated, the invention also encompasses cellulases having amino acid sequences including conservative amino acid substitutions. Such substitutions are well known in the art.

Cth10H6 has significant amino acid homology to cellulases and β-gluacanases. BLASTP searches revealed that Cth10H6 was homologous to Chain B of the *Acidothermus cellulolyticus* Endocellulase (34% amino acid identity and 49% amino acid similarity over 350 amino acids). Cth10H6 also showed limited homology to *C. thermocellum* dockerin domains with about 40% amino acid identity and about 65% amino acid similarity in the region from amino acid 440-495 of Cth10H6. The BLAST search also found homology with several β-glucanases in the N-terminal regions of Cth10H6 with about 20% amino acid identity and about 45% similarity over about 150 amino acids. A BLASTP search for conserved domains demonstrated that Cth10H6 has similarity to cellulases in the region from amino acid 12-355 of the protein and to endoglucanases in the region from amino acid 11-380. The homology information suggested that Cth10H6 was a novel protein that would have both cellulase and β-glucanase activity. Regions of Cth10H6 that may be suited to conservative modification, such as amino acid substitution or deletion, which do not substantially affect the activity of Cth10H6 may include at one or more of positions 1-8, 18-22, 53-60, 81-89, 124-133, 173-180, 225-240, 283-295, 318-227, 335-343, 368-382, 385-393, 399-412 and 414-443 of SEQ ID NO:1. Amino acid pairs that may be more amenable for substitution are known in the art, and are described, for example, in French and Robson, J. of Mol. Evolution 19(2):171-175 (1983), *Protein Engineering A Practical Approach*, A. R. Rees, M. J. E. Sternberg, and R. Wetzel, editors, Oxford University Press, Oxford, 1992, and *Directed Enzyme Evolution Screening and Selection Methods*, F. H. Arnold and G. Georgiou, editors, Humana Press, Totowa, N.J. 2003, the disclosures of which are hereby incorporated by reference in their entireties. Other substitutions may also be made without substantially affecting the activity of Cth10H6. Methods for making amino acid deletions or substitutions are well known in the art, and are described, for example, in *Protein Engineering A Practical Approach*, A. R. Rees, M. J. E. Sternberg, and R. Wetzel, editors, Oxford University Press, Oxford, 1992, and *Directed Enzyme Evolution Screening and Selection Methods*, F. H. Arnold and G. Georgiou, editors, Humana Press, Totowa, N.J. 2003. The polypeptides produced by substitution/modification can be screened for cellulase activity in crude preparations, or in purified form, according to the Examples disclosed herein.

The purified cellulases of the invention suitably exhibit endoglucanase activity, exoglucanase activity, or combinations thereof. Endoglucanase activities exhibited by cellulases of the invention suitably include beta-glucanase, cellulase and/or endoxylanase activity. Exoglucanase activities exhibited by cellulases of the invention suitably includes exocellulase activity. The purified cellulases of the invention show activity using insoluble celluloses, soluble cellulose derivatives, or beta-glucans, or combinations thereof, as substrates. As will be appreciated, activity of a cellulase may be determined by any method known in the art. For example, endo- or exo-glucanase activity may be determined by incubating enzyme with commercially available fluorescent test substrates and detecting fluorescence using automated methods or direct visualization. Alternatively, enzyme activity may be detected by measuring reducing sugars using, for example, a commercially available chromogenic assay. As another alternative, oligomeric sugars can be hydrolyzed to monomeric sugars, which in turn, may be measured by high performance liquid chromatography (HPLC). Suitably, thermostable enzymes, including thermostable cellulases, retain at least about 70% of activity, at least about 75% of activity, at least about 80% of activity, at least about 85% of activity, at least about 90% of activity, or at least about 95% of activity when the enzyme is incubated at 60° C. in a suitable medium for 60 minutes.

The invention also provides DNA constructs useful in preparing the cellulases of the invention. The DNA constructs include at least one polynucleotide encoding the polypeptides described herein, operably connected to a promoter. As used herein, a promoter includes an expression control sequence near the start site of transcription. A promoter may optionally include distal enhancer or repressor elements which may be non-contiguous with the start site of transcription. The promoter may be a "heterologous" promoter, i.e., a promoter not natively associated with the coding sequence. The promoter may be constitutive or inducible. A "constitutive" promoter is a promoter that is active under most environmental and developmental conditions. An "inducible" promoter is a promoter that is under environmental or developmental regulation.

For example, for constitutive expression in plants, the 35S-CaMV, the maize ubiquitin 1, and the rice actin 1 promoter may be used (Franck et al., 1980, Cell 21: 285-294, Christensen et al., 1992, Plant Mo. Biol. 18: 675-689; Zhang et al., 1991, Plant Cell 3: 1155-1165). Plant organ-specific promoters may include a promoter from storage sink tissues such as seeds, potato tubers, and fruits, for example, (Edwards and Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter or the cruA promoter from *Brassica napus*, or any other seed specific promoter known in the art.

For example, for expression in bacteria or other cells, inducible promoters such as the $P_L$ promoter, the tac promoter, the trp promoter and the trc promoter may be suitable. Other examples of suitable promoters for directing the transcription of the DNA sequence encoding Cth10H6 cellulase, including expression in a bacterial host, may include one or more of the promoters of the lac operon of *E. coli*, the *Streptomyces coelicolor* agarase gene dagA, the *Bacillus licheniformis* alpha-amylase gene (amyL), the *Bacillus stearothermophilus* maltogenic amylase gene (amyL), the *Bacillus amiyloliquefaciens alpha*-amylase gene (amyQ), and the *Bacillus subtilis* xyIA and xyIB genes.

The term "operably connected" refers to a functional linkage between a regulatory sequence (such as a promoter) and a second nucleic acid sequence, wherein the regulatory sequence directs transcription of the nucleic acid corresponding to the second sequence. A coding sequence for Cth10H6 is shown in SEQ ID NO:2.

The polynucleotide constructs may suitably be introduced into host cells, such as *E. coli* or other suitable hosts known in the art, for producing cellulases of the invention. Other suitable host cells may include fungal cells, such as yeast or filamentous fungal cells. Methods of introducing polynucleotide constructs into host cells are well known in the art, as are expression systems. The polynucleotide constructs may be introduced into the host cells using vectors that are maintained in the host cell cytoplasm, or may be integrated into the genome of the host cell.

In some embodiments, the host cell is a recombinant plant cell. The recombinant plant cell may suitably be used to produce a transgenic plant that expresses a cellulase of the invention. As will be appreciated, expression of a cellulase by a plant containing cellulosic material can eliminate processing steps in methods of producing cellulose byproducts from the transgenic plant. Suitably, the cellulase may be released upon mechanical or chemical disruption of the transgenic plant cell in a reaction mixture and will become available to hydrolyze cellulose to cellobiose without the need for first expressing and purifying the enzyme in, e.g., a bacterial expression system. Most suitably, the growth properties of the transgenic plant will not be adversely affected by the expression of the cellulase. This may be accomplished by targeting the transgene to particular cells or tissues using cell or tissue specific promoters, for example, a promoter for a seed storage protein. The polynucleotide construct may be expressed in seeds, as described in U.S. Pat. No. 7,033,627, or in chloroplasts, as described in U.S. Pat. No. 6,680,426. These patents are incorporated herein by reference in their entireties.

In some embodiments, the cellulase of the invention may be included in a composition. Compositions including the cellulase may optionally include further enzymes useful in processing plant material, such as beta-glucosidase, alpha-amylase and glucoamylase. Optionally, any or all of the enzymes used in such compositions may be thermostable. For example, thermostable beta-glucosidases are well known in the art, see, e.g., Zverlow W et al., *Microbiology*, 143: 3537-3542 (1997); Kengen et al., *Eur. J. Biochem.* 213:305-312; Wang X et al., *J. Bacteriol.* 185(4): 4248-55 (2003); Wright R M et al., *Appl. and Env. Microbiol.*, 58(11): 3455-3465 (1992); and Breves, R et al., *Appl. and Env. Microbiol.*, 63(10): 3902-10 (1997), the disclosures of which are incorporated herein by reference in their entireties.

The invention also provides a method of producing a cellulose byproduct. The method includes a step of contacting a cellulosic material with the cellulase of the invention to produce a first byproduct. Suitably the first byproduct is cellobiose. The method optionally comprises a step of contacting the cellobiose with a beta-glucosidase to produce a soluble sugar. Suitably, the beta-glucosidase is thermostable Suitably, the soluble sugar produced by action of the beta-glucosidase is glucose. In a further optional step, the glucose is fermented to produce a second byproduct. Suitably, the second byproduct is ethanol, lactic acid or acetone. Suitable reaction conditions for the steps of the method may be determined by skilled artisans, however, in some embodiments, the step of contacting the cellulosic material with the cellulase of the invention is carried out at a temperature of about 40° C. to about 70° C. More suitably, the temperature is about 50° C. to about 65° C. Most suitably, the temperature is about 60° C. to about 65° C. In some embodiments, the step of contacting the cellulosic material with the cellulase of the invention is carried out at a pH of about 4.0 to about 6.0. More suitably, the pH is about 4.5 to about 5.0.

An additional embodiment of the invention provides a method of producing ethanol. The first step in the method is to contact a cellulosic material with the cellulase of the invention under conditions sufficient to produce cellobiose. Suitably, the conditions include a temperature of about 40° C. to about 70° C., more suitably about 50° C. to about 65° C., most suitably, about 60° C. to about 65° C. and a pH of about 4.0 to about 6.0, more suitably about 4.5 to about 5.0. The duration of incubation will vary depending upon the amount of cellulose in the cellolosic material, the amount of cellulase and other factors, and may be determined by the skilled artisan by routine optimization. Suitably the cellulases of the invention are provided at at least about 0.5 mg, at least about 1 mg, at least about 2 mg, at least about 5 mg, or at least about 10 mg per gram of cellulose/cellulosic material. Suitably the cellulase of the invention is provided at less than about 150 mg, less than about 100 mg, less than about 50 mg, less than about 30 mg or less than about 20 mg per gram of cellulose/ cellulosic material. Suitably, the duration of the incubation is at least about 4 hours, at least about 8 hours, at least about 12 hours, at least about 18 hours or at least about 24 hours. Suitably, the duration of the incubation is less than about 144 hours, less than about 132 hours, less than about 120 hours, less than about 108 hours or less than about 96 hours. Suitably, the incubation is carried out at at least about 40° C., at least about 45° C., at least about 50° C., at least about 55° C., or at least about 60° C. Suitably, the incubation is carried out at less than about 85° C., less than about 80° C., less than about 75° C., less than about 70° C., or less than about 65° C. In a second step of the method, the cellobiose produced in the first step is contacted with a beta-glucosidase under conditions sufficient to produce glucose. A third step includes fermenting the glucose under conditions sufficient to produce ethanol. Suitable conditions for the second and third steps may be determined by the skilled artisan.

Suitably, in the methods of producing ethanol, the cellolosic material is a plant material. The plant material is optionally wood, corn, sorghum (milo), barley, wheat, oat, rice or cotton. The plant material may also be a paper or a textile.

EXAMPLES

The following examples are provided to assist in a further understanding of the invention. The particular materials and conditions employed are intended to be further illustrative of the invention and are not limiting on the reasonable scope of the appended claims.

Example 1

Materials and Methods

*Clostridium thermocellum* cultures were a kind gift of Dr. Paul Weimer, USDA Agricultural Research Service, U.S. Dairy Forage Research Center, University of Wisconsin, Madison, Wis. For generation of DNA libraries, cultures were concentrated by centrifugation. The cell concentrate was lysed using a combination of SDS and proteinase K, and genomic DNA was purified using phenol/chloroform extraction. The genomic DNA was precipitated, treated with RNase to remove residual contaminating RNA, and fragmented by hydrodynamic shearing (HydroShear apparatus, GeneMachines, San Carlos, Calif.) to generate fragments of 2-4 kb. The fragments were purified on an agarose gel, end-repaired, and ligated into pEZSeq, a lac promoter vector (Lucigen, Middleton, Wis.).

To express putative cellulases, the *C. thermocellum* library was transformed into electrocompetent *E. coli* cells (Lucigen). Individual colonies were picked and grown in 96 well blocks. Aliquots of the cultures were collected by centrifugation and lysed using CELLYTIC IIB reagent (Sigma). The lysates were assayed for cellulase activity at 70° C. in 0.200 ml of 50 mM acetate buffer, pH 5.8 containing 0.2% AZCL-HE-Cellulose (Megazyme).

Cellulase activity was further characterized by measuring the amount of reducing sugars released from cellulose using 2,2-bicinchoninic-acid, as described by Kenealy et al., Biotechnology Letters 25: 1619-1623 (2003), incorporated herein by reference. Substrate specificity for endo-activities was measured using AZCL-labeled and azo-labeled insoluble substrates (Megazyme). Substrate specificity for exo-activity was determined using 4-methylumbelliferyl-β-D-cellobioside, 4-methylumbelliferyl-β-D-xylopyranoside, 4-methyl umbelliferyl-β-D-glucoyranoside and 5-bromo-6-chloro-3-indolyl-β-D-glucopyranoside (Magenta-β-D-glucopyranoside).

Example 2

Identification of Cth10H6

During screening of the *Clostridium thermocellum* DNA library for cellulytic activity, a previously undescribed endoglucanase, designated Cth10H6, was discovered. Extracts of a 10-ml culture of the clone were used to characterize the cloned enzyme, which showed strong activity on an insoluble beta-glucan substrate (AZCL-barley-beta-glucan, Megazyme), and shows some activity against dye-linked cellulose substrates and 4-methylumbelliferyl-β-D-cellobioside, a soluble cellulase substrate.

Sequencing of the ends of the DNA insert allowed identification of the gene product within the *C. thermocellum* genome. The gene encodes a putative 57 kDa protein, having the predicted sequence shown in SEQ ID NO: 1. SEQ ID NO: 1 represents the full-length functional Cth10H6 protein without the leader sequence which is cleaved in vivo. The full-length Cth10H6 translation product including the 32 amino acid leader sequence is shown in SEQ ID NO: 5. The coding sequence for the translation product of SEQ ID NO: 5 is shown in SEQ ID NO: 6.

Example 3

Cloning of Cth10H6

Using 50 nanograms of template plasmid DNA, the cellulase gene was amplified using the expression primers CTH10H6 L: CCGAACAATGACGACTGGCTGCATG TTGAAGGT (SEQ ID NO: 3) and CTH10H6 R: TCT-TCTCTGCGGCCGCTTATATT GGTATTTTAAG-CACTTTCCTCT (SEQ ID NO: 4). The N-terminal primer was designed to begin at the consensus signal-sequence cleavage site, between amino acids 32 and 33 of the full-length translation product of Cth10H6. The amplified PCR product was digested with Not1 enzyme to produce a Not1 blunt-ended fragment and cloned into the pTACST3 NotI blunt vector (Lucigen). The ligated product was then transformed into 10G F' competent cells (Lucigen) and the transformed clones were selected on kanamycin plates. The pTACST3 NotI blunt vector introduced a nine-amino acid, MTQDPSRVG (SEQ ID NO: 7) affinity tag at the N terminus. Cloning was also done in PET vectors to determine the impact of the affinity tag on activity of Cth10H6. The affinity tag was found to not impact the activity of Cth10H6. Eight transformants were picked and grown in 50 ml cultures; four of these produced active enzyme. The active clones were identified as described in Example 1 and cell mass collected by centrifugation.

Example 4

Purification of Cth10H6

Cells from the four cultures produced in Example 3 were resuspended in 50 mM Tris-HCl, pH 8.0, pooled and lysed by sonication. The lysate was clarified by centrifugation and *E. coli* proteins were precipitated by heat treatment at 65° C. for 20 minutes. The heat-treated lysate was clarified by centrifugation and applied to a 15 ml Q SEPHAROSE Fast Flow column (GE Amersham) equilibrated with 50 mM Tris-HCl, pH 8.0. The column was washed with 50 ml of 50 mM Tris-HCl, pH 8.0, and Cth10H6 was eluted with a 200 ml gradient of 0 to 500 mM NaCl in 50 mM Tris-HCl, pH 8.0. Active fractions were pooled, concentrated to 1.0 ml and applied to a 150 ml SEPHACRYL S-100 High Resolution column (GE Amersham) equilibrated with 50 mM Tris-HCl, pH 8.0. Active fractions were pooled and concentrated to 1.0 ml for characterization studies.

Native gel electrophoresis was used to verify the identity of the purified protein as a cellulase. Electrophoresis was performed on 1× and 3× concentrations using either a 15% acrylamide or 4-20% gradient acrylamide gel. After completion of electrophoresis, the gel was incubated at 60° C. for 60 minutes in 50 mM acetate buffer, pH 5.8, containing 1 mM 4-methylumbelliferyl-β-D-cellobioside. The gel was photographed under a UV light to show activity of the cellulase (FIG. 1, left panel), then stained with Coomassie Brilliant Blue R-250 and destained (FIG. 1, right panel). The results, shown in FIG. 1, show that the pooled, purified active enzymes exhibited cellulase activity. In FIG. 1, the pair of lanes marked 'A' in each panel represent clarified *E. coli* lysate at 1× (left) and 3× (right), the pair of lanes marked 'B' in each panel represent heat-treated, clarified lysate at 1× (left) and 3× (right), the pair of lanes marked 'C' in each panel represent Q SEPHAROSE concentrate at 1× (left) and 3× (right), the pair of lanes marked 'D' in each panel represent SEPHACRYL S-100 concentrate at 1× (left) and 3× (right).

Figure 2:
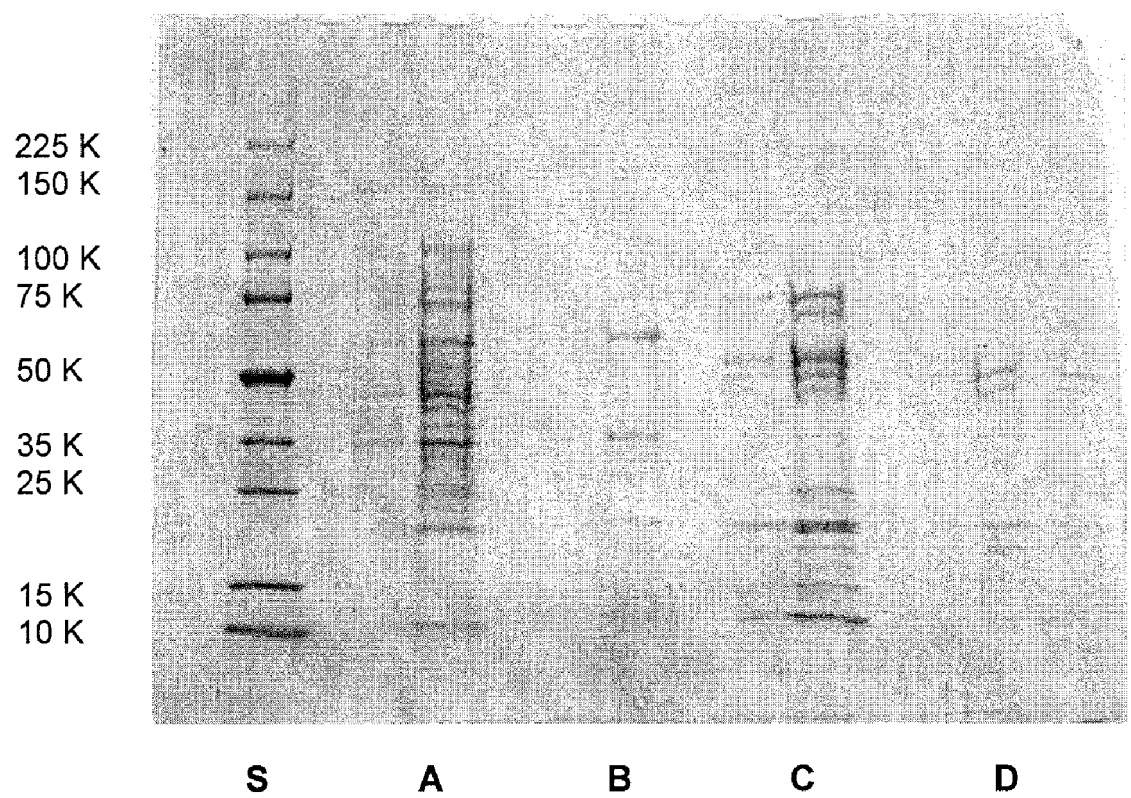
FIG. 2 is a photograph of an SDS-PAGE gel showing the separation of proteins recovered during the expression and isolation of the cellulase, as described in the Examples.

SDS denaturing gel electrophoresis was used to verify the purity and size of the cellulase. Electrophoresis was performed on a 4-20% gradient acrylamide gel. The results, shown in FIG. 2, show an approximately 57 kDa band in all fractions. In FIG. 2, the lane marked 'S' represents Promega Broad Range Molecular Weight Markers, the pair of lanes marked 'A' represent clarified *E. coli* lysate at 1× (left) and 3× (right), the pair of lanes marked 'B' represent heat-treated, clarified lysate at 1× (left) and 3× (right), the pair of lanes marked 'C' represent Q SEPHAROSE concentrate at 1× (left) and 3× (right), the pair of lanes marked 'D' represent SEPHACRYL S-100 concentrate at 1× (left) and 3× (right).

Example 5

Characterization of Cth10H6

Cellulose binding capabilities. Cellulose, 100 mg, (Sigma 310697 or C6429) was incubated with 1.00 ml of 50 mM acetate buffer, pH 5.8, containing 10 µg of enzyme protein for three hours at room temperature. The cellulose was removed by centrifugation and residual, soluble enzyme was assayed in 0.50 ml of 50 mM acetate buffer, pH 5.8 containing 0.2% AZCL-HE-Cellulose. Less than 1% of the initial enzyme dosage was not bound to the cellulose; no difference was seen between cellulose products in binding.

Temperature and pH optima. The temperature optimum of Cth10H6 was determined in 0.50 ml of 50 mM acetate buffer, pH5.8, containing 0.2% AZCL-beta-glucan and 1.0 µg of enzyme protein. Assays were performed at 1000 rpm, for 20 minutes in a Thermomixer R (Eppendorf). Tubes were clarified by centrifugation and absorbance values determined using a $EL_x800$ plate reader (Bio-Tek). Cth10H6 had a sharp temperature optimum at 65° C.; the activity of the enzyme dropped to less than 20% of this maximum value at 70° C.

The pH optimum of Cth10H6 was determined in 0.50 ml of 50 mM acetate buffer, containing 0.2% AZCL-HE-cellulose and 1.0 µg of enzyme protein. Assays were performed at 1000 rpm, for 30 minutes in a Thermomixer R (Eppendorf). Tubes were clarified by centrifugation and absorbance values determined using a BIO-TEK $EL_x800$ plate reader. Cth10H6 exhibited activity over the pH range of 4.0 to 6.0, with maximum activity between pH 4.5 and 5.0.

Cellulase specific activity. The specific activity of Cth10H6 purified according to Example 4, and shown in FIG. 1, lane D, was determined at 60° C., pH 4.5, in a Thermomixer R (Eppendorf) agitating at 1000 rpm, using a 10% suspension of a 20 µm microcrystalline cellulose powder (commercially available from Sigma as 310697) as the substrate. Reducing sugars were measured using Pierce BCA reagent with glucose as standard. A value of 0.6 micromoles reducing equivalents/minute/mg protein was obtained. The specific activity of Cth10H6 was also determined using a 1.0% solution of a carboxymethylcellulose, sodium salt (commercially available from Sigma as C4888) as the substrate. A value of 36 micromoles reducing equivalents/minute/mg protein was obtained.

Endogluconase specificity. The endogluconase specificity of Cth10H6 was determined in 0.50 ml of 50 mM acetate buffer, pH 5.8, containing 0.2% insoluble substrate (as listed below in Table 1) and 1.0 µg of enzyme protein. Assays were performed at 60° C., 1000 rpm, for 20 minutes in a Thermomixer R (Eppendorf, Westbury, N.Y.). Tubes were clarified by centrifugation and absorbance values determined using an $EL_x800$ plate reader (Bio-Tek).

TABLE 1

Endoglucanase Activity of Cth10H6

| Enzyme Activity | Substrate | Relative Activity |
|---|---|---|
| Beta-glucanase | AZCL-beta-glucan (Megazyme) | 100% |
| EndoCellulase | AZCL-HE-Cellulose (Megazyme) | 58% |
| Endo-xylanase | AZCL-xylan (Megazyme) | 4% |
| Arabinoxylanase | AZCL-arabinoxylan (Megazyme) | <1% |
| Mannanase | AZCL-galactomannan (Megazyme) | <1% |
| Cellulase | Azo-Avicel (Megazyme) | <1% |

Exogluconase specificity. The exogluconase specificity of Cth10H6 was determined in 0.50 ml of 50 mM acetate buffer, pH 5.8, containing 10 mM substrate (as listed below in Table 2) and 1.0 µg of enzyme protein, or by spotting enzyme directly on agar plates containing 10 mM substrate. Identical results were obtained with both methods. Liquid assays were performed at 60° C., 1000 rpm, for 120 minutes in a Thermomixer R (Eppendorf, Westbury, N.Y.). Tubes and plates were examined using a hand-held UV lamp and compared to negative and positive controls.

TABLE 2

Exoglucanase Activity of Cth10H6

| Enzyme Activity | Substrate | Relative Activity |
|---|---|---|
| Exo-cellulase | 4-methylumbelliferyl-β-D-cellobioside | Strong Positive |
| Beta-xylosidase | 4-methylumbelliferyl-β-D-xylopyranoside | Negative |
| Beta-glucosidase | 4-methylumbelliferyl-β-D-glucopyranoside | Negative |
| | 5-bromo-6-chloro-3-indolyl-β-D-glucopyranoside | Negative |

Prophetic Example 6

Production of Cth10H6 from Transformed Bacteria

A culture of *Bacillus subtilis* is transformed using a conventional competent cell method with a pUB110 plasmid encoding the antibiotic resistance protein, kanamycin phosphotransferase and containing the *B. stearothermophilus alpha*-amylase promoter sequence, the *B. stearothermophilus alpha*-amylase leader sequence, the sequence encoding the first seven N-terminal amino acids of the mature *B. stearothermophilus alpha*-amylase enzyme followed by the polynucleotide encoding Cth10H6. Positive transformants are selected for on plates containing 20 μg/ml kanomycin and 1% cellulose. Transformants are cultured in shake flask medium as follows:

Shake flask medium for seed development is prepared to contain the following (g/L):

| | |
|---|---|
| Bio Springer yeast extract | 6.0 |
| Cargill soy flour | 45.0 |
| $K_2HPO_4$ | 3.25 |
| $KH_2PO_4$ | 1.875 |
| Corn Products corn syrup 1632* | 60.0 |

*Sterilized separately and is added after cooling; before inoculation 20 μg/ml kanomycin is added to each flask.

Shake flasks are run with 150 ml medium/500 ml flask at 37° C. and 180 rpm.

Fermentations are run in 7.5 liter New Brunswick fermentors with 4.0 liters of medium. The fermentor medium contains the following (g/L):

| | |
|---|---|
| Bio Springer yeast extract | 3.5 |
| Cargill soy flour | 25.0 |
| $K_2HPO_4$ | 0.6 |
| $MgSO_4$ | 1.875 |
| $MnCl_2$ | 0.1 |
| $CaCl_2$ | 1.0 |
| $FeSO_4$ | 0.05 |
| Dextrose* | 40.0 |

*Sterilized separately and added after cooling; before inoculation 20 μg/ml kanomycin is added to each fermentor.

Fermentors are fed with 1.6 g/l-hr. of dextrose and the pH is maintained between 6.8 and 6.9 by addition of ammonia. Fermentations are carried out for 72-94 hours at 37° C. and 0.5 vvm aeration to yield cellulase protein. Fermentation is clarified by filtration through diatomaceous earth, and the clarified filtrate ultrafiltered to 1/10 the original volume.

Prophetic Example 7

Production of Ethanol Using Cth10H6

Cellulosic material (a hardwood residue, milled to <0.1 mm particle diameter) is mixed with Cth10H6 produced according to Example 6. The cellulosic material is adjusted to 30% dry matter by addition of water and the pH of the slurry adjusted to 5.0 by addition of acid or base. Cth10H6 is added at 10 mg enzyme/gram cellulosic material. Thermostable xylanase is added at 1.0 mg enzyme/gram cellulosic material and thermostable beta-glucosidase is added at 10 mg enzyme/gram cellulosic material. The material is heated to 60° C. and mixed using a screw extruder for a residence time of 48 to 96 hours. After completion of the reaction, the mixture is cooled to 30° C. and dry brewers yeast is added at a dosage of 1.0 g/L. The alcohol fermentation is conducted at 30° C. for 72 hr. After fermentation, the ethanol formed is recovered by distillation under atmospheric pressure.

It is specifically contemplated that any embodiment of any method or composition of the invention may be used with any other method or composition of the invention.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

What is claimed is:

1. A purified thermostable cellulase comprising an amino acid sequence having at least 90% identity to SEQ ID NO: 1, wherein the cellulase exhibits endoglucanase or exoglucanase activity, or combinations thereof.

2. The cellulase of claim 1, wherein the cellulase is active in soluble form.

3. The cellulase of claim 1, comprising an amino acid sequence having at least 95% identity to SEQ ID NO: 1.

4. The cellulase of claim 1, comprising the amino acid sequence shown in SEQ ID NO: 1.

5. The cellulase of claim 1, wherein the cellulase exhibits beta-glucanase activity.

6. The cellulase of claim 1, wherein the cellulase exhibits exo-cellulase activity.

7. A composition comprising the cellulase of claim 1.

8. The composition of claim 7, further comprising an enzyme selected from a β-glucosidase, an alpha-amylase, or a glucoamylase, or combinations thereof.

9. A method of producing at least one cellulose byproduct comprising contacting a cellulosic material with the cellulase of claim 1.

10. The method of claim 9, wherein a first byproduct is cellobiose.

11. The method of claim 10, further comprising contacting the cellobiose with a β-glucosidase to produce glucose.

12. The method of claim 11, wherein the β-glucosidase is thermostable.

13. The method of claim 11, further comprising fermenting the glucose to produce a second byproduct.

14. The method of claim 13, wherein the second byproduct is ethanol, lactic acid, or acetone.

15. The method of claim 9, wherein the method comprises contacting the cellulosic material with the cellulase at a temperature of about 40° C. to about 70° C.

16. The method of claim 9, wherein the method comprises contacting the cellulosic material with the cellulase at a pH of about 4.0 to about 6.0.

17. A method of producing ethanol comprising:
a) contacting a cellulosic material with the cellulase of claim 1 to produce cellobiose;
b) contacting the cellobiose with a β-glucosidase to produce glucose; and
c) fermenting the glucose to produce ethanol.

18. The method of claim 17, wherein the cellulosic material is a plant material.

19. The method of claim 17, wherein the plant material is selected from the group consisting of wood, corn, sorghum, barley, wheat, oat, rice and cotton.

20. The method of claim 17, wherein the cellulosic material is a paper or a textile.

* * * * *